United States Patent
Malinowski et al.

(10) Patent No.: US 8,091,321 B2
(45) Date of Patent: Jan. 10, 2012

(54) METHOD FOR PACKAGING SURGICAL SUTURES

(75) Inventors: Stan Malinowski, Guilford, CT (US); Mario Santangelo, Berlin, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 5 days.

(21) Appl. No.: 12/572,381

(22) Filed: Oct. 2, 2009

(65) Prior Publication Data

US 2010/0018164 A1    Jan. 28, 2010

Related U.S. Application Data

(62) Division of application No. 11/396,776, filed on Apr. 3, 2006, now Pat. No. 7,600,634.

(51) Int. Cl.
*B65B 63/04* (2006.01)

(52) U.S. Cl. .............. 53/430; 53/462; 206/63.3

(58) Field of Classification Search ............. 53/429, 53/430, 445, 460, 462, 472, 477, 118, 397; 206/63.3, 227, 380, 338, 495, 382

See application file for complete search history.

(56) References Cited

U.S. PATENT DOCUMENTS

| | | |
|---|---|---|
| 3,162,307 A | 12/1964 | Regan, Jr. |
| 3,951,261 A | 4/1976 | Mandel et al. |
| 4,369,880 A | 1/1983 | Giggey et al. |
| 4,412,614 A | 11/1983 | Ivanov et al. |
| D272,600 S | 2/1984 | Kubas |
| 4,533,041 A * | 8/1985 | Aday et al. ............. 206/63.3 |
| 4,555,016 A | 11/1985 | Aday et al. |
| 4,572,363 A | 2/1986 | Alpern |
| 4,574,948 A | 3/1986 | Huck et al. |
| 4,574,957 A | 3/1986 | Stead |
| 4,579,221 A | 4/1986 | Corella |
| 4,615,435 A | 10/1986 | Alpern et al. |

(Continued)

FOREIGN PATENT DOCUMENTS

DE      19706729      8/1998

(Continued)

*Primary Examiner* — Hemant M Desai

(57) ABSTRACT

A surgical suture package for storing at least one surgical suture includes an outer jacket having a plurality of panels foldably connected to each other and adapted to fold upon each other to form an inner pocket and an inner retainer for positioning within the pocket of the outer jacket. The inner retainer includes a row of support panels having a main support panel for supporting the at least one suture, and a pair of side support panels foldably connected to the main support panel along respective opposed major sides of the main support panel. The side support panels are adapted to be folded onto the main support panel to at least partially enclose the at least one suture. A cover panel is foldably connected to the main support panel along a minor side of the main support panel, and is adapted to be folded onto the support panels. A row of closure panels including a main closure panel is foldably connected to the main support panel along a second minor side of the main closure panel, and a pair of side closure panels is foldably connected to the main closure panel along respective opposed major sides of the main closure panel. The main closure panel is adapted to be folded along the second minor side of the main support panel onto the main support panel and the side closure panels are adapted to be folded along the major sides of the main closure panel to at least partially enclose the support and cover panels.

12 Claims, 10 Drawing Sheets

U.S. PATENT DOCUMENTS

| | | | |
|---|---|---|---|
| 4,674,629 A | 6/1987 | Gunselman | |
| 4,691,825 A | 9/1987 | Schmetz et al. | |
| 4,699,271 A | 10/1987 | Lincoln et al. | |
| 4,700,833 A | 10/1987 | Smith | |
| 4,708,241 A | 11/1987 | Black | |
| 4,730,725 A | 3/1988 | Marshall, Sr. et al. | |
| 4,813,537 A | 3/1989 | Okuhara | |
| 4,821,878 A | 4/1989 | Jones | |
| 4,884,681 A | 12/1989 | Roshdy et al. | |
| 4,887,710 A | 12/1989 | Roshdy et al. | |
| 4,896,767 A | 1/1990 | Plnheiro | |
| 4,946,043 A | 8/1990 | Roshdy et al. | |
| 5,024,322 A | 6/1991 | Holzwarth | |
| 5,024,323 A | 6/1991 | Bolton | |
| 5,048,678 A | 9/1991 | Chambers | |
| 5,078,730 A | 1/1992 | Li et al. | |
| 5,086,914 A | 2/1992 | Mish et al. | |
| 5,092,455 A | 3/1992 | Leary | |
| 5,101,968 A | 4/1992 | Henderson et al. | |
| 5,121,836 A | 6/1992 | Brown et al. | |
| 5,123,528 A | 6/1992 | Brown et al. | |
| 5,127,518 A | 7/1992 | Holzwarth et al. | |
| 5,131,534 A | 7/1992 | Brown et al. | |
| 5,154,283 A | 10/1992 | Brown | |
| 5,174,087 A | 12/1992 | Bruno | |
| 5,199,561 A | 4/1993 | Roshdy | |
| 5,228,565 A | 7/1993 | Sinn | |
| 5,236,082 A | 8/1993 | Brown | |
| 5,249,673 A | 10/1993 | Sinn | |
| 5,261,210 A | 11/1993 | Brown | |
| 5,271,494 A | 12/1993 | Odermatt et al. | |
| 5,277,299 A | 1/1994 | Holzwarth et al. | |
| 5,279,411 A | 1/1994 | Brunken | |
| 5,301,801 A | 4/1994 | Sinn | |
| 5,335,783 A | 8/1994 | Sinn | |
| 5,341,922 A | 8/1994 | Cerwin et al. | |
| 5,348,146 A | 9/1994 | Sterling et al. | |
| 5,350,060 A | 9/1994 | Alpern et al. | |
| 5,353,922 A | 10/1994 | Sinn | |
| 5,358,102 A | 10/1994 | Brown | |
| 5,358,624 A | 10/1994 | Roshdy et al. | |
| 5,359,831 A * | 11/1994 | Brown et al. | 53/430 |
| 5,366,081 A | 11/1994 | Kaplan et al. | |
| 5,386,912 A | 2/1995 | Holzwarth et al. | |
| 5,392,903 A | 2/1995 | Sinn | |
| 5,425,445 A | 6/1995 | Brown et al. | |
| 5,427,243 A | 6/1995 | Roshdy | |
| 5,433,315 A | 7/1995 | Brandau | |
| 5,435,438 A | 7/1995 | Scanlon | |
| 5,437,362 A | 8/1995 | Sinn | |
| 5,439,102 A * | 8/1995 | Brown et al. | 206/63.3 |
| 5,460,263 A | 10/1995 | Brown et al. | |
| 5,461,844 A | 10/1995 | Brown | |
| 5,487,469 A | 1/1996 | Roshdy et al. | |
| 5,494,154 A | 2/1996 | Ainsworth et al. | |
| 5,529,175 A | 6/1996 | Brunken | |
| 5,533,611 A | 7/1996 | Bordignon et al. | |
| 5,538,132 A | 7/1996 | Propp et al. | |
| 5,555,976 A | 9/1996 | Pemot | |
| 5,560,477 A | 10/1996 | Scanlon | |
| 5,566,821 A | 10/1996 | Brown et al. | |
| 5,566,822 A | 10/1996 | Scanlon | |
| 5,582,288 A * | 12/1996 | Zatarga | 206/63.3 |
| 5,584,164 A | 12/1996 | Sinn | |
| 5,601,185 A | 2/1997 | Behring et al. | |
| 5,675,961 A * | 10/1997 | Cerwin et al. | 53/430 |
| 5,692,602 A | 12/1997 | Bordignon et al. | |
| 5,746,311 A * | 5/1998 | Brown et al. | 206/63.3 |
| 5,762,816 A | 5/1998 | Brown et al. | |
| 5,769,214 A | 6/1998 | Zatarqa | |
| 5,788,063 A | 8/1998 | Van Ness | |
| 5,819,918 A | 10/1998 | Scanlon | |
| 5,871,089 A * | 2/1999 | Odermatt | 206/63.3 |
| 5,896,982 A | 4/1999 | Surcin et al. | |
| 6,015,042 A | 1/2000 | Cerwin et al. | |
| 6,029,805 A | 2/2000 | Alpem et al. | |
| 6,029,806 A | 2/2000 | Cerwin et al. | |
| 6,045,035 A | 4/2000 | Murakami | |
| 6,080,184 A | 6/2000 | Peters et al. | |
| 6,138,440 A * | 10/2000 | Gemma | 53/430 |
| 6,234,327 B1 | 5/2001 | Reed | |
| 6,237,757 B1 | 5/2001 | Alpem et al. | |
| 6,260,696 B1 | 7/2001 | Braginsky et al. | |
| 6,598,737 B2 | 7/2003 | Rudnick | |
| 6,659,270 B2 | 12/2003 | Williamson, IV et al. | |
| 6,719,128 B2 | 4/2004 | Alpem et al. | |
| 6,739,450 B2 | 5/2004 | Roshdy et al. | |
| 6,915,623 B2 * | 7/2005 | Dey et al. | 53/478 |
| 6,938,755 B2 * | 9/2005 | Braginsky et al. | 206/63.3 |
| 7,637,369 B2 * | 12/2009 | Kennedy et al. | 206/63.3 |
| 2002/0175091 A1 | 11/2002 | Williamson, IV et al. | |
| 2003/0006149 A1 | 1/2003 | Rudnick | |
| 2003/0029737 A1 | 2/2003 | Alpem et al. | |
| 2003/0178325 A1 | 9/2003 | Roshdy et al. | |
| 2004/0020795 A1 | 2/2004 | Braginsky et al. | |
| 2007/0245688 A1* | 10/2007 | Detruit et al. | 53/167 |
| 2009/0120037 A1* | 5/2009 | Detruit et al. | 53/167 |

FOREIGN PATENT DOCUMENTS

| | | |
|---|---|---|
| DE | 19706739 | 8/1998 |
| EP | 557059 | 2/1993 |
| EP | 577993 | 6/1993 |
| EP | 494637 | 6/1995 |
| EP | 418059 | 11/1996 |

* cited by examiner

METHOD FOR PACKAGING SURGICAL SUTURES

CROSS REFERENCE TO RELATED APPLICATION

This application is a divisional of U.S. patent application Ser. No. 11/396,776, filed Apr. 3, 2006, now U.S. Pat. No. 7,600,634 issued on Oct. 13, 2009, the disclosure of which is hereby incorporated by reference herein, in its entirety.

TECHNICAL FIELD

The present disclosure relates generally to surgical suture packaging, and, more particularly, relates to a foldable suture package for retaining at least on suture.

BACKGROUND

Surgical packages for sutures with attached needles are widely known in the art. Two commonly used suture packages include a molded plastic retainer and a folded paper retainer. A conventional molded plastic retainer incorporates a molded channel, e.g., a racetrack channel, for receiving a plurality of sutures and a needle park for mounting the needles attached to the sutures. The folded paper retainer is generally constructed from paperboard, fiberboard or other suitable material, and incorporates a plurality of panels which are folded to form an envelope in which the wound suture(s) is placed.

While molded plastic retainers can receive a number of sutures with attached needles of various sizes, the folded paper retainers are generally more cost effective and less wasteful than the plastic retainers. However, drawbacks of conventional folded paper retainers include difficulties in opening the retainer, and in accessing and removing the stored sutures. In addition, if several sutures are stored in a folded paper retainer, these sutures have a tendency to tangle if provisions are not made to maintain the sutures separated.

SUMMARY

Accordingly, the present disclosure relates to improvements in surgical suture packaging. In one preferred embodiment, a surgical suture package for storing at least one surgical suture includes an outer jacket having a plurality of panels foldably connected to each other and adapted to fold upon each other to form an inner pocket and an inner retainer for positioning within the pocket of the outer jacket. The inner retainer includes a row of support panels having a main support panel for supporting the at least one suture, and a pair of side support panels foldably connected to the main support panel along respective opposed major sides of the main support panel. The side support panels are adapted to be folded onto the main support panel to at least partially enclose the at least one suture. A cover panel is foldably connected to the main support panel along a minor side of the main support panel, and is adapted to be folded onto the support panels. A row of closure panels including a main closure panel is foldably connected to the main support panel along a second minor side of the main closure panel, and a pair of side closure panels is foldably connected to the main closure panel along respective opposed major sides of the main closure panel. The main closure panel is adapted to be folded along the second minor side of the main support panel onto the main support panel and the side closure panels are adapted to be folded along the major sides of the main closure panel to at least partially enclose the support and cover panels.

Means for retaining the side closure panels in a folded condition at least partially enclosing the support and cover panels may be provided. Alternatively, the side closure panels include a tab and slot arrangement for releasably retaining the side closure panels in a folded condition at least partially enclosing the support and cover panels.

The outer jacket includes at least two outer panels foldably connected to each other to define the pocket. Preferably, the outer jacket includes a row of three outer panels foldably connected to each other to define the pocket. The outer panels include a central outer panel and side outer panels foldably connected to respective major sides of the central outer panel. The side outer panels include a tab and slot arrangement for retaining the outer panels in a folded condition. The side outer panels may be each connected to the central outer panel through a gusset. The outer jacket further may include a top panel connected to a minor side of one of the side outer panels. The top panel is adapted to fold along an intermediate fold line thereof to substantially enclose the pocket formed by the outer enclosure. The top panel may include a locking slit dimensioned to receive a minor side of the other of the side panel or central outer panel.

The cover panel of the inner retainer may include a suture receiving slot for receiving and supporting a suture end portion of the at least one suture. Alternatively, a suture clip is attachable to the at least one suture. A plurality of sutures may be supported within the inner retainer whereby the suture clip is connected to each end portion of the sutures.

The suture package may include an outer envelope which defines a pouch for receiving the inner retainer member and the outer jacket in the folded conditions thereof.

In another preferred embodiment, a suture package for a plurality of surgical needled sutures includes first and second rows of panels. The first row includes a main support panel for supporting a plurality of needled sutures, and a pair of side support panels foldably connected to the main support panel along respective opposed major sides of the main support panel, whereby the side support panels are adapted to be folded onto the main support panel to at least partially enclose the sutures. The second row includes a cover panel foldably connected to the main support panel along a first minor side of the main support panel and adapted to be folded onto the support panels. A suture clip is attachable to each of the suture end portions, preferably, proximal of the needles to permit concurrent removal of the sutures from the support panels.

The suture package may include a third row having a plurality of closure panels. The closure panels include a main closure panel foldably connected to the main support panel along a second minor side of the main closure panel, and a pair of side closure panels foldably connected to the main closure panel along respective opposed major sides of the main closure panel. The main closure panel is adapted to be folded along the second minor side of the main support panel onto the cover panel and the side closure panels are adapted to be folded along the major sides of the main closure panel to at least partially enclose the support and cover panels.

An outer jacket may be provided. The outer jacket has at least two outer panels foldably connected to each other and adapted to fold upon each other to form an inner pocket. The inner pocket is adapted to at least partially accommodate the support, cover and closure panels in a folded condition thereof. The outer jacket preferably includes three panels.

A method of packaging a plurality of sutures is also disclosed.

BRIEF DESCRIPTION OF THE DRAWINGS

Preferred embodiments of the present disclosure will be better appreciated by reference to the drawings wherein.

DESCRIPTION OF THE PREFERRED EMBODIMENTS

Figure 1:
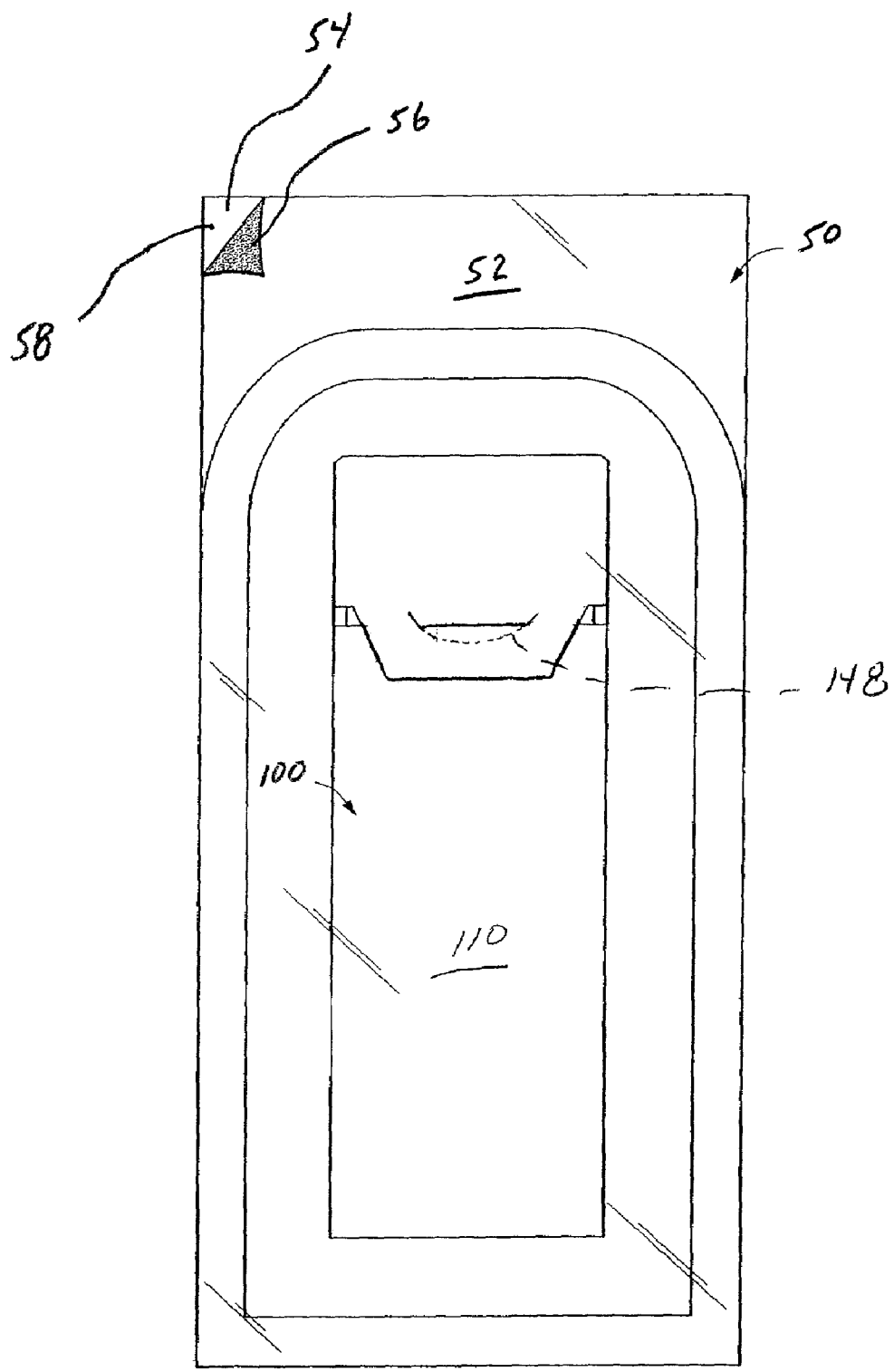
FIG. 1 is a front plan view of a suture package including an envelope, a foldable outer jacket and a foldable inner retainer constructed in accordance with the principles of the present disclosure.
Figure 2:
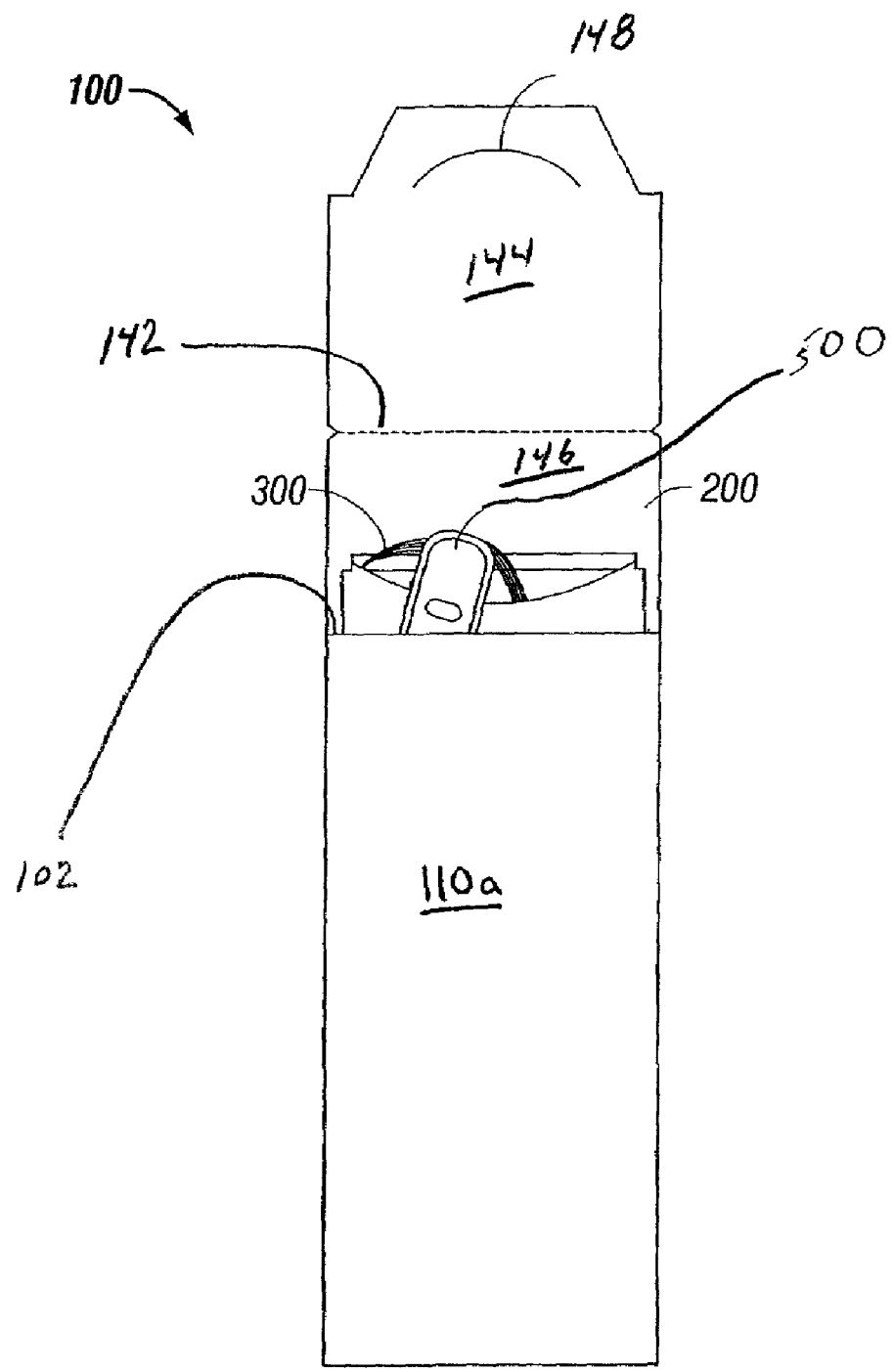
FIG. 2 is a front plan view of the outer jacket with the inner retainer positioned within the pocket of the outer jacket.

Referring now to the drawings wherein like reference numerals illustrate similar components throughout the several views, FIGS. 1-2 illustrate the suture package in accordance with the present disclosure depicted generally as reference numeral 10. Suture package 10 includes envelope 50, outer jacket 100 and inner retainer 200 which is secured within the outer jacket 100. Envelope 50 receives outer jacket 100 and inner retainer 200 when the outer jacket 100 and the inner retainer 200 are in their respective folded conditions. In FIG. 2, envelope 50 is removed.

Envelope 50 includes top sheet 52 and bottom sheet 54. Top sheet 52 may be formed of a clear plastic, such as a polyethylene, or other like material. Bottom sheet 54 may be constructed from paperboard, fiberboard, Tyvek®, aluminum foil or other like material. The materials of construction of top and bottom sheets 52, 54 preferably prevent or greatly impede the transmission of moisture therethrough. Top sheet 52 and bottom sheet 54 are generally rectangular in shape and substantially the same size. Sheets 52, 54 are adhered together along their respective peripheries by an adhesive, cement, etc. or the like. In one preferred embodiment, a peripheral line of peelable adhesive is used. Sheets 52, 54 define flaps 56, 58 at one corner, which are devoid of adhesive. Flaps 56, 58 remain unattached to be readily grasped by the operator to facilitate at least partial separation of sheets 52, 54 when opening envelope 50. Envelope 50 hermetically seals outer jacket 100 and inner retainer 200, preventing contaminates from reaching the stored sutures 300 and, as mentioned above, minimizing passage of moisture. Outer jacket 100 is visible through top sheet 52 of envelope 50 as depicted in FIG. 1.

Figure 3:
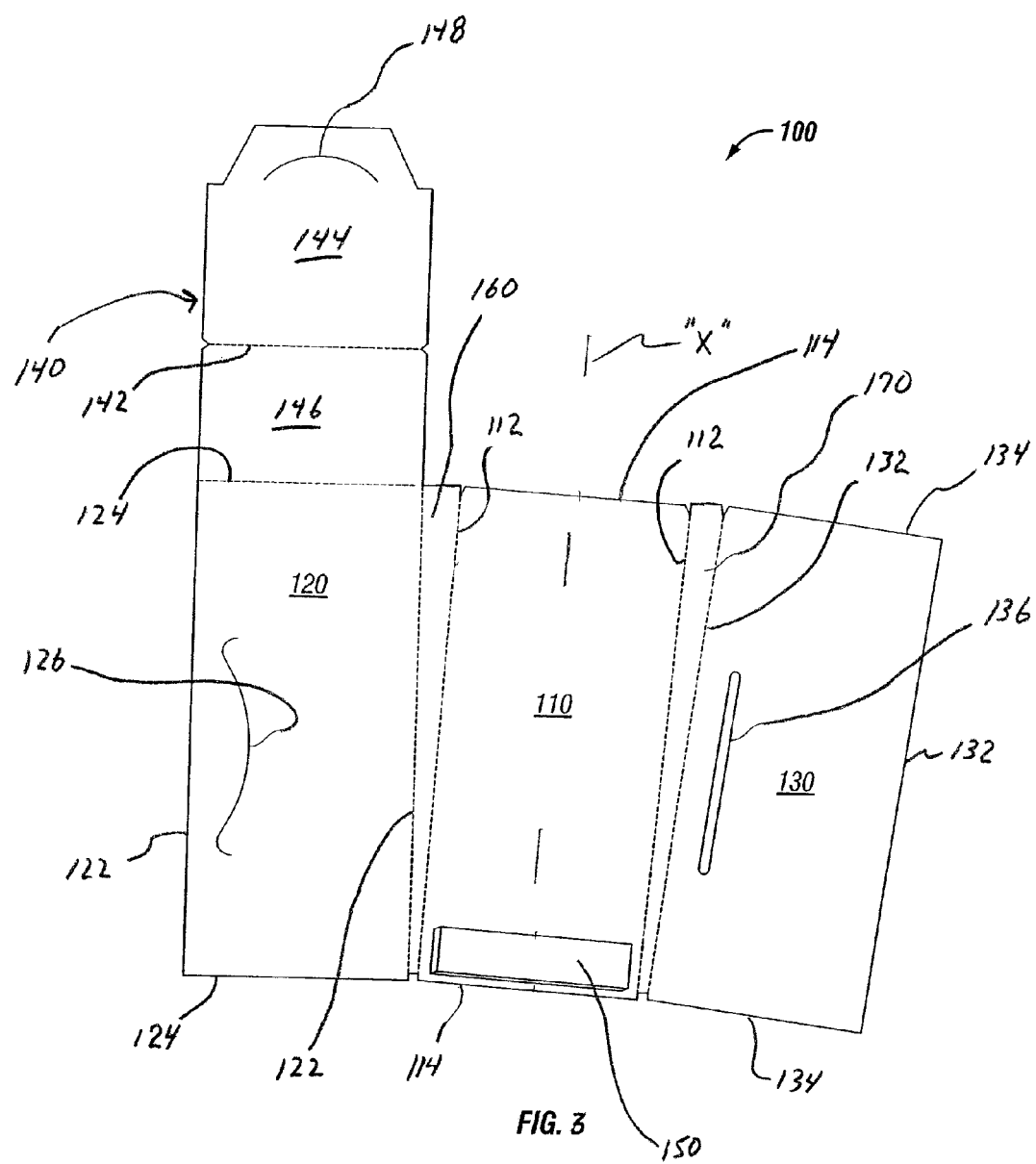
FIG. 3 is a front plan view of the outer jacket in an unfolded condition.

With reference to FIGS. 2-3, outer jacket 100 will be discussed. Outer jacket 100 defines inner pocket 102 when in the folded condition to receive folded inner retainer 200. In FIG. 3, outer jacket 100 is shown in a flat, unfolded or pre-folded state. Outer jacket 100 may be constructed from paperboard, fiberboard, cardboard or any other fibrous material such as Tyvek®, or like material. Outer jacket 100 is preferably die cut to form a series of interconnected panels. Specifically, outer jacket 100 includes panels 110, 120, 130 and top panel 140. Panels 110, 120, 130 are generally rectangular in shape and substantially the same size. Panels 110, 120, 130 each have respective opposed major sides 112, 122, 132 also referred to as longitudinal edges with reference to reference longitudinal axis "x", and respective opposed minor sides 114, 124, 134, also referred to as transverse edges. Centrally positioned panel 110 includes a foam strip 150 adjacent its lower minor side 114. Foam strip 150 functions as a stop when inner retainer 200 is inserted within pocket 102 of folded outer jacket 100. Foam strip 150 may also maintain the folded panels 120, 130 a desired or predetermined distance from centrally positioned panel 110. Panel 130 includes longitudinal slot 136 along one major side 132 adjacent centrally positioned panel 110. Panel 120 includes tab 126 formed therein. Tab 126 is dimensioned to cooperate with longitudinal slot 136 to releasably secure panels 110, 130 thereby securing the panels 110, 120, 130 a folded condition.

Gussets 160, 170 respectively interconnect panels 120, 130 and centrally positioned panel 110. Gussets 160, 170 are substantially triangular in shape tapering inwardly toward the lower end of outer jacket 110. Gussets 160, 170 prevent panels 120, 130 from collapsing onto, and contacting panel 110 when the panels 120, 130 are folded onto the panel 110. Gussets 160, 170 also provide depth to the folded outer jacket 100 thereby increasing the size of pocket 102 formed by folded panels 110, 120, 130. Gussets 160, 170 define double fold lines corresponding to major sides 112, 122, 132 about which panels 120, 130 fold onto centrally positioned panel 110. The triangular or tapering configuration of gussets 160, 170 ensures that pocket 102 has a greater depth adjacent the upper or open end of outer jacket 100 and a lesser depth toward the lower end of outer jacket 100. This arrangement permits folded inner retainer 200 to be readily inserted into pocket 102 while ensuring that the inner retainer 200 is frictionally engaged within the pocket 102 adjacent the lower end of the outer jacket 100.

With continued reference to FIGS. 2-3, top panel 140 is foldably connected to panel 120 along upper minor side 124 of the panel 120. In this regard, top panel 140 may be folded backwards to expose the contents within outer jacket 100. Top panel 140 includes intermediate fold line 142 which thereby defines upper top panel portion 144 and lower top panel portion 146. Top panel portion 144 is adapted to fold along fold line 142 onto top panel portion 146 to enclose the pocket 102 defined by outer jacket 100. Top panel portion 144 includes arcuate slit 148 which is configured and dimensioned to receive upper minor side 114 of panel 110 or upper minor side 134 of panel 130 to secure top panel 140 in a folded condition.

Figure 4:
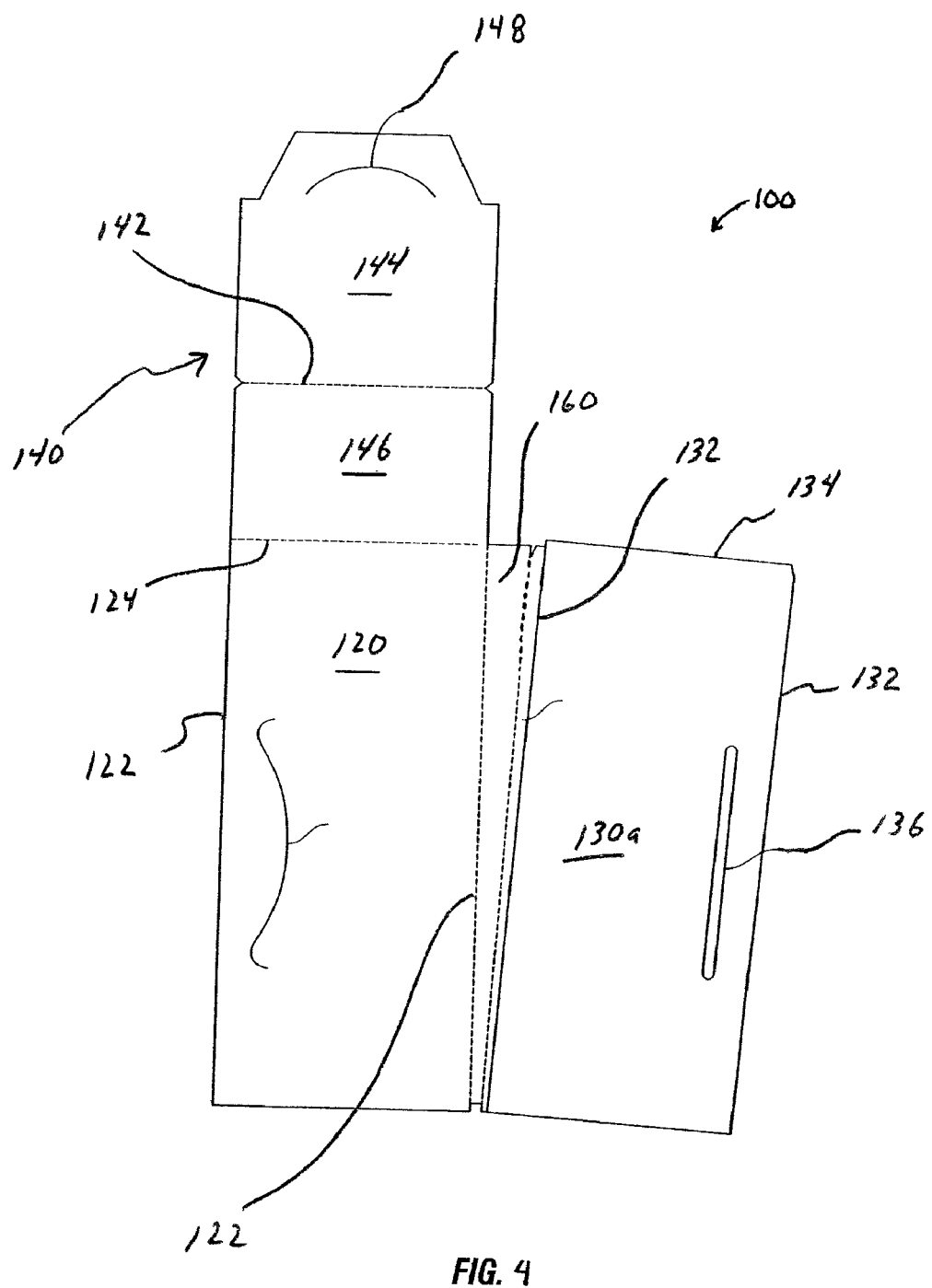
FIGS. 4-6 are plan views illustrating the preferred sequence of folding the outer jacket to form the pocket.
Figure 5:
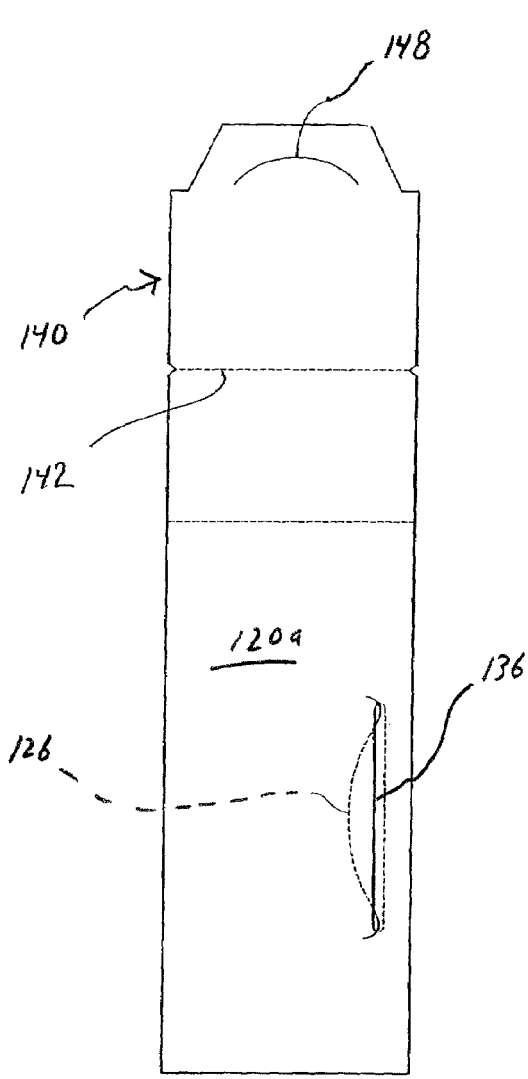
Figure 6:
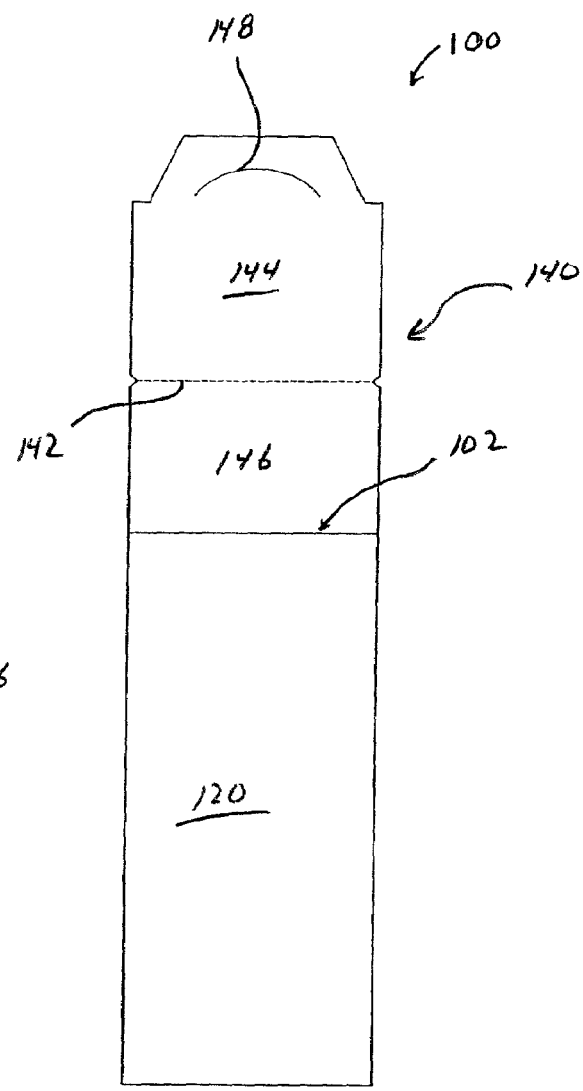

The process of folding outer jacket 100 to form pocket 102 for receiving inner retainer 200 will be described in detail. Initially, with reference to FIG. 3, panel 130 is folded along major side 132 onto panel 110 such that the rear surface 130a of the panel 130 is exposed as depicted in FIG. 4. Thereafter, panel 120 is folded along major side 122 onto panels 110, 130 such that rear surface 120a of the panel 120 is exposed as shown in FIG. 5. (Alternatively, panels 110, 130 may be folded onto panel 120.) With panels 110, 120, 130 folded onto each other, tab 126 of panel 120 is then inserted into slot 136 of panel 130 to releasably secure the panels 120, 130. FIG. 6 illustrates the front side of outer jacket 100 with top panel 140 in an open position and pocket 102 accessible for reception of the folded inner retainer 200.

Figure 7:
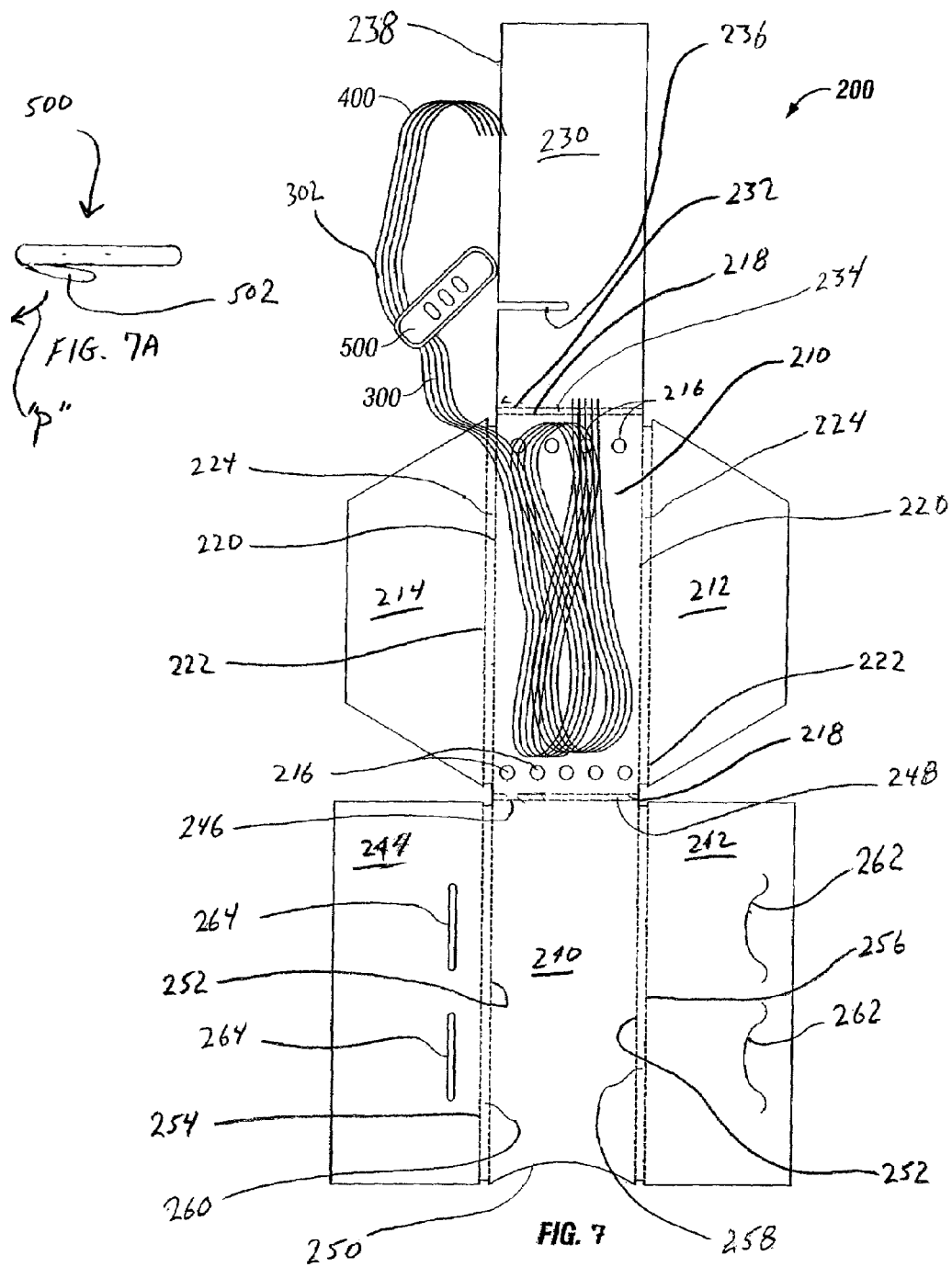
FIG. 7 is a front plan view of the inner retainer in an unfolded condition.

Referring now to FIG. 7, inner retainer 200 will be discussed. Inner retainer 200 is shown in a flat, unfolded or pre-folded state. Inner retainer 200 is constructed from paper or any other like material identified hereinabove in connection with outer jacket 100. Inner retainer 200 includes a first or central row of support panels, namely, centrally positioned main support panel 210, and side support panels 212, 214 on each side of the main support panel 210. Main support panel 210 defines openings 216 adjacent upper and lower minor sides 218 of the main support panel 210. Openings 216 are sized and configured to receive winding pins or pegs of a winding device (not shown). Sutures 300 may be wound about the winding pins either manually or through automated means. Main support panel 210 is generally rectangular in configuration defining major sides 220 and minor sides 218. Side support panels 212, 214 are generally trapezoidal in shaped and have major sides 222 which are interconnected to major sides 220 of main support panel 210 through gusset 224. Gussets 224 define double fold lines corresponding to major sides 220, 222 about which side support panels 212, 214 fold onto main support panel 210. Gussets 224 increase the depth of the folded support panels to thereby provided sufficient space to store sutures 300.

Inner retainer 200 further includes cover panel 230 which forms a second row of panels of the inner retainer 200. Cover panel 230 includes minor side 232 which is connected to upper minor side 218 of main support panel 210 through gusset 234. Gusset 234 defines a double fold line about which panel 230 folds onto main support panel 210. Cover panel 230 may have suture receiving slot 236 extending from a peripheral edge (e.g., major side 238) of the cover panel 230 into the central area of the cover panel 230. Suture receiving slot 234 may be utilized to receive end portions of sutures 300 to assist supporting the suture end portions and attached needles 400 within inner retainer 200 as will be discussed. Alternatively, suture receiving slot 236 may receive suture clip 500 which is attached to the end portions of sutures 300. As a further alternative, cover panel 230 may be devoid of suture receiving slot 236.

Inner retainer 200 further includes a third row of closure panels, namely, central closure panel 240 and a pair of side closure panels 242, 244 connected to the central closure panel 240. Central closure panel 240 is connected along minor side 246 to minor side 218 of main support panel 210 through gusset 248. Gusset 248 defines a double fold line about which central panel 242 folds onto main support panel 210. Central closure panel 242 defines an arcuate or recessed lower minor side 250. The recessed configuration of minor side 250 assists in exposing the stored needles 400 of the assembled package as will be discussed. Central closure panel 242 further defines major sides 252. Side closure panels 242, 244 include major sides 254, 256, and are connected to central closure panel 242 through gussets 258, 260 respectively. Gussets 258, 260 each define double fold lines. Side closure panels 242, 244 include tabs 262 and slots 264 respectively. Slots 264 of side panel 244 are sized to receive tabs 262 of side panel 242 to facilitate retaining the side closure panels 242, 244 in a folded condition.

The preferred sequence of loading inner retainer 200 with sutures 300 and folding the inner retainer 200 will be discussed. Initially, pre-folded inner retainer 200 is placed on a winding device such that openings 216 are aligned with and receive winding pegs of the winding device (not shown). Individual sutures 300 with attached needles 400 are wound around the winding pegs either manually or through an automated suture winding process. Sutures 300 may be wrapped around the winding pegs collectively as a bundle, or individually. Preferably, sutures 300 have suture clip 500 attached to the suture end portions 302 adjacent needles 400. Suture clip 500 retains the sutures in a bundle and preferably in spaced relation to minimize tangling of the suture ends 302. Suture clip 500 also permits sutures 300 to be removed from inner retainer 200 as a bundle rather than as individual sutures.

Suture clip 500 may be attached to the individual sutures 300 prior to or subsequent to the winding process. In one preferred embodiment depicted in FIG. 7A, suture clip 500 includes resilient finger 502. Resilient finger 502 may be displaced or pivoted away from suture clip 500 as shown by directional arrow "p" to receive sutures 300. Preferably, finger 502 has sufficient resiliency to return to its normal position to frictionally engage sutures 300. Other arrangements for suture clip 500 are also envisioned including separately mounted clamps, an aperture, a slit extending through the suture clip 500, etc. Once sutures 300 have been wound onto the winding pegs, the winding pegs may be removed and inner retainer 200 may be folded.

Figure 8:
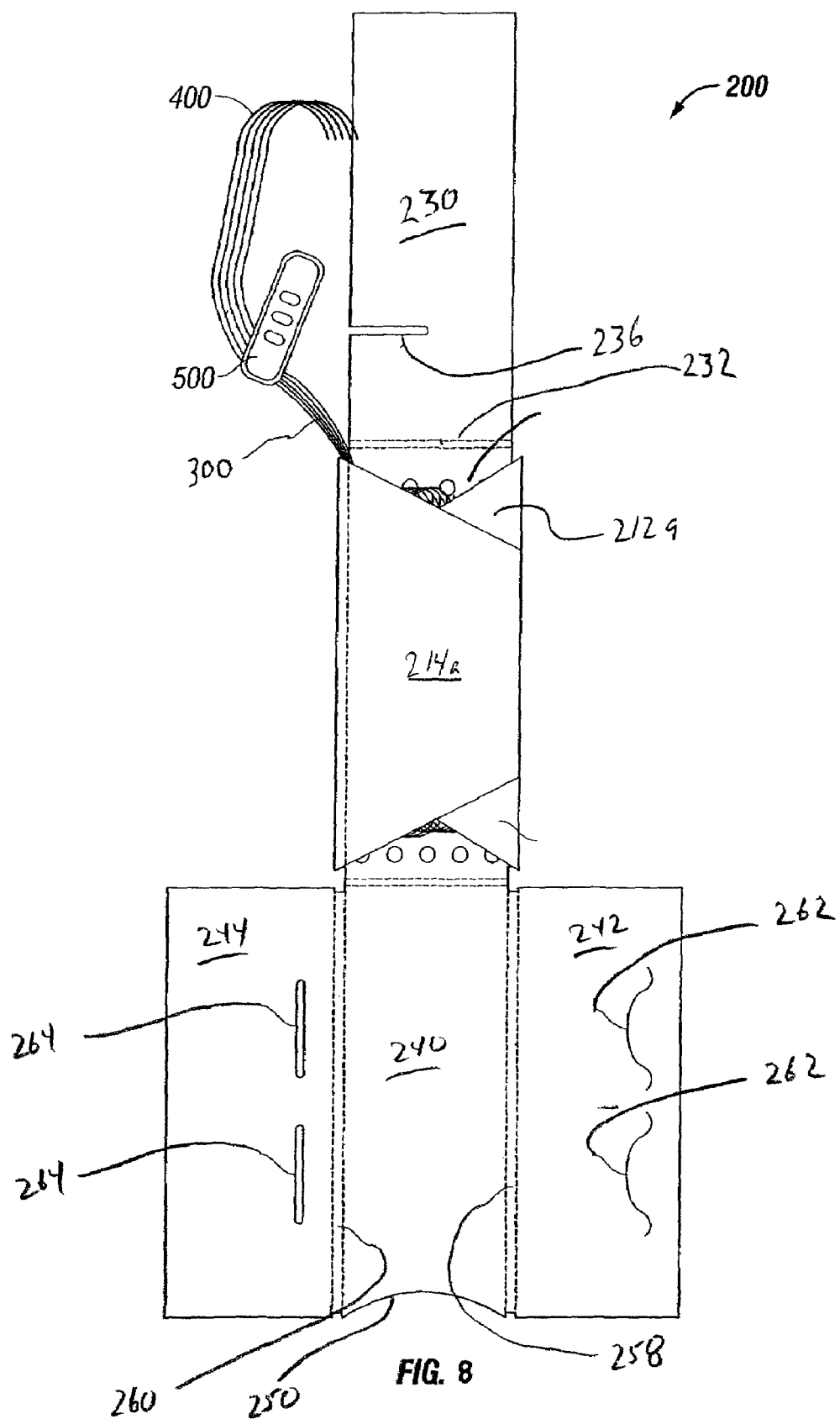
FIGS. 8-12 are plan views illustrating the preferred sequence of loading and folding the inner retainer to form a suture compartment for a plurality of sutures.

Once sutures 300 are in position supported by central support panel 210 as shown in FIG. 7, side support panel 212 is folded along the double fold line sides defined by gusset 220 onto the central support panel 210. Side support panel 214 is then along the double fold line defined by gusset 224 onto the rear side 212a of side support panel 212 to expose the rear side 214a of the side support panel 214. FIG. 8 illustrates side support panels 212, 214 in their folded conditions on central support panel 210. As appreciated, gussets 224 provide sufficient depth to the folded support panels 210, 212, 214 to accommodate the loaded sutures 300.

Figure 9:
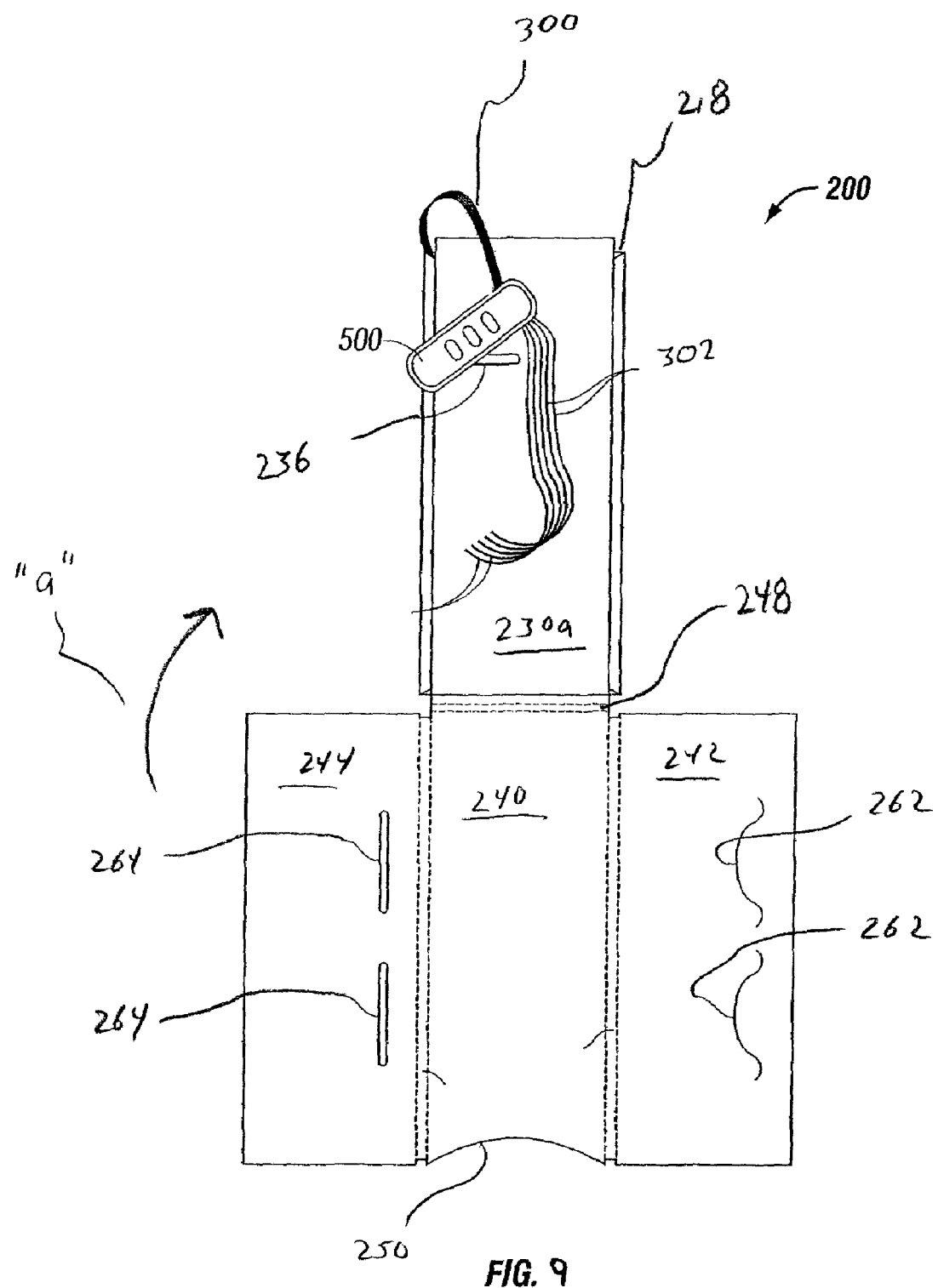
Figure 9A:
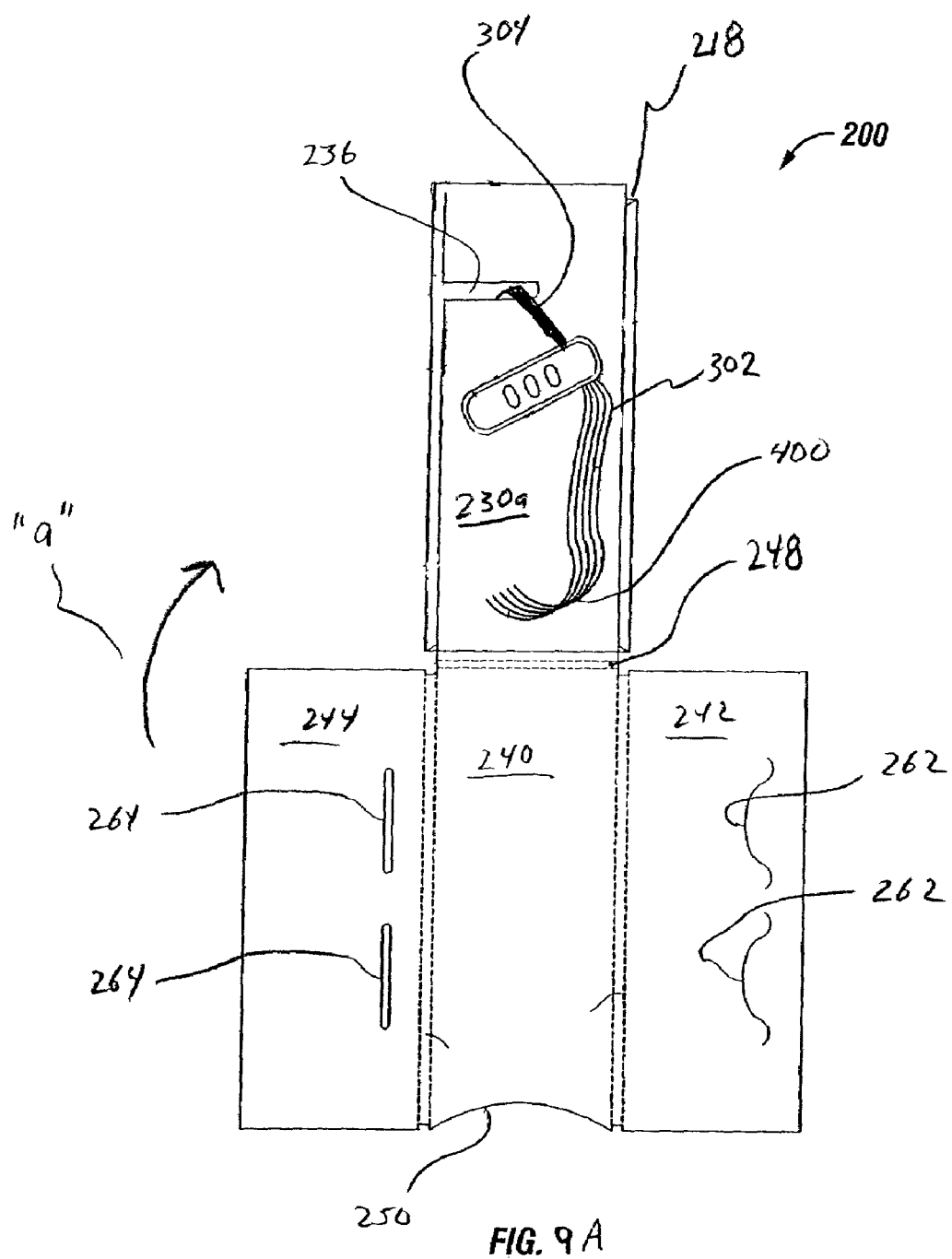

With reference to FIG. 9, cover panel 230 is folded onto main support panel 210 to cover the wound sutures 300 with the exception of the suture end portions 302 adjacent the attached needles 400 and suture clip 500. Suture clip 500 and attached needles 400 are preferably positioned on the rear side 230a of cover panel 230 and preferably hung in suspension over minor side 218 of main support panel 210. In the alternative, clip 500 may be manipulated to engage suture receiving slot 236 of cover panel 230. As a further alternative, individual suture portions 304 on the side of suture clip 500 away from needles 400 are passed through suture receiving slot 236 of cover panel 230 and cover panel 230 is folded onto main support panel 210 as depicted in FIG. 9A. In this manner, suture receiving slot 236 supports the individual sutures 300 with attached needles 400 and suture clip 500 in suspended manner against rear side 230a of cover panel 230.

Figure 10:
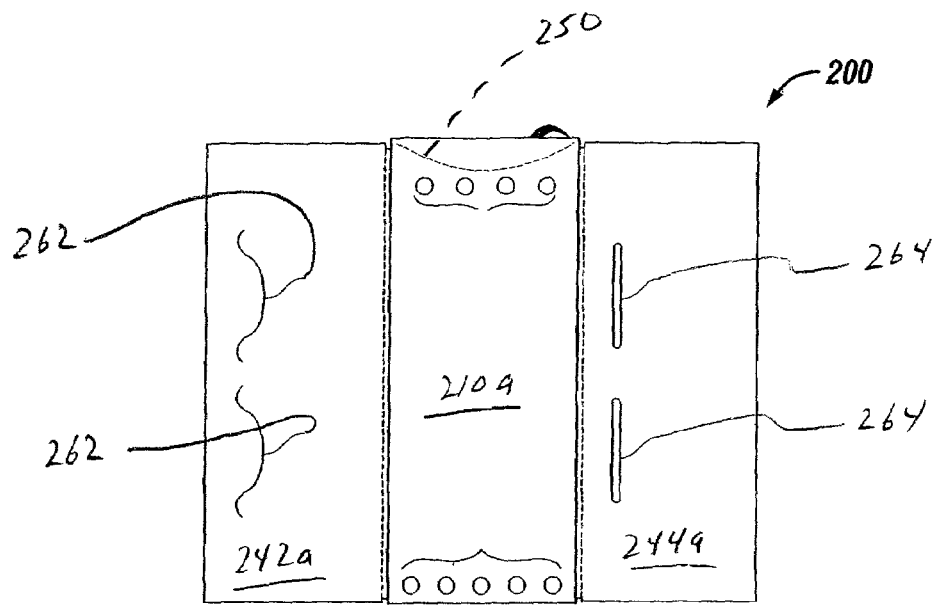
Figures 11, 12:
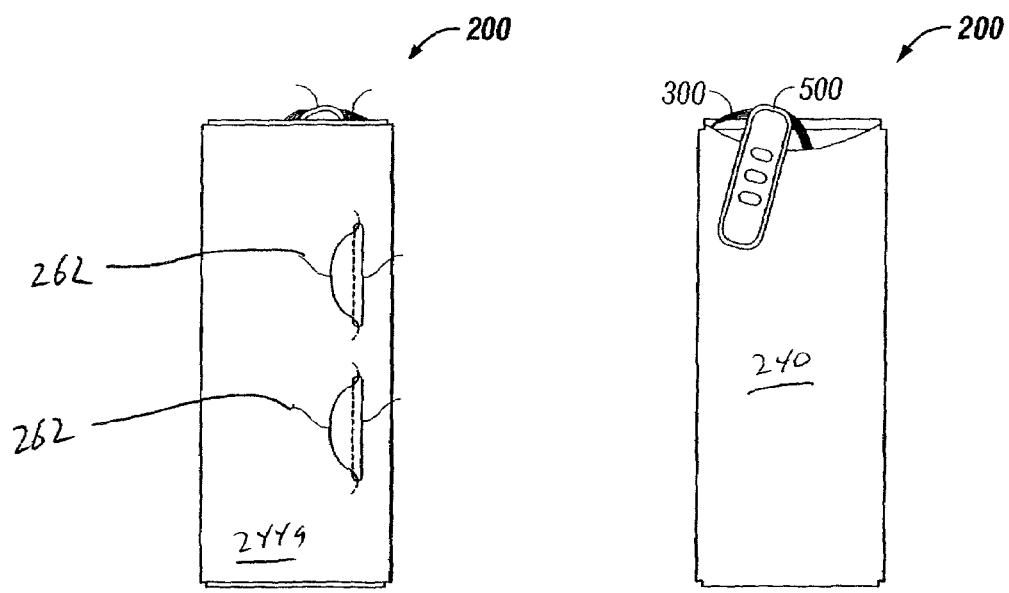

Once cover panel 230 is in position, central closure panel 240 is folded in the direction of the arrow "a" of FIG. 9 along the double fold line provided by gusset 248 onto the rear side 230a of cover panel 230. FIG. 10 illustrates central closure panel 240 in the folded condition. In FIG. 10, the rear side 210a of needle support panel 210 is shown. Side closure panels 242, 244 are then folded around main support panel side 210 and tabs 262 are inserted within slots 264 to secure the side closure panels 242, 244 together as depicted in FIG. 11. Preferably, suture clip 500 is manipulated to hang over the arcuate minor side 250 to provide enhanced access to the suture clip 250, and attached needles 400 and sutures 300 as depicted in FIG. 12.

Referring again to FIG. 2, inner retainer 200 is then positioned within pocket 102 of outer jacket 100 and advanced to a position where the outer jacket 100 frictionally engages the inner retainer 200 and/or the inner retainer 200 abuts foam strip 150. Top panel portion 144 is folded along fold line 142 onto top panel portion 146. In the folded position, tab 148 of panel portion 144 engages the top minor side 114 of panel 110, thus securing inner retainer 200 within outer jacket 100. Finally, inner retainer 200, securely contained within outer jacket 100, is sealed within outer envelope 50.

In order to access suture bundle 300, outer envelope 50 is opened by separating flaps 54, 56. Next, tab 148 of cover panel 140 is disengaged from the top minor side 114 of panel 110 and panel 140 is folded back along fold line 124. Inner retainer 200 is then removed from pocket 102 of outer jacket 100. Panels 242, 244 are then unfolded first by disengaging tabs 262 of panel 242 from slots 264 of panel 244. Suture bundle 300 is thus accessible and may be removed as a bundle using suture clip 500. Removal of the sutures 300 as a bundle greatly minimizes the potential of suture tangling which would otherwise exist if the sutures were removed individually. If desired, the remainder of inner retainer 200 may be unfolded prior to removing the sutures 300.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims append hereto.

What is claimed is:

1. A method of packaging at least one suture, the method comprising the steps of:
    providing an inner retainer member including:
        a row of support panels having a main support panel and a pair of side support panels foldably connected to the main support panel along respective opposed major edges of the main support panel; and
        a cover panel foldably connected to the main support panel along a minor edge of the main support panel;
    placing a plurality of sutures on the main support panel of the row of support panels;
    attaching a suture clip to each suture end portion of the sutures;
    folding the side support panels along the major edges onto the main support panel to at least partially enclose the sutures;
    folding the cover panel along the minor edge of the main support panel whereby the cover panel at least partially covers the support panels; and
    positioning the suture end portions and the suture clip adjacent a rear side of the support panel such that the suture end portions and the suture clip are accessible.

2. The method according to claim 1 wherein the inner retainer member includes a row of closure panels, the closure panels including a main closure panel foldably connected to the main support panel along a second minor edge of the main closure panel, and a pair of side closure panels foldably connected to the main closure panel along respective opposed major edges of the main closure panel and further including the step of folding the main closure panel along the second minor edge of the main support panel onto the main support panel and folding the side closure panels along the major edges of the main closure panel to at least partially enclose the support and cover panels.

3. The method according to claim 2 wherein the main closure panel defines a recessed minor side.

4. The method according to claim 1 wherein the step of placing includes winding a plurality of sutures on the main support panel.

5. The method according to claim 1 further including the step of providing an outer jacket, the outer jacket including a plurality of outer panels foldably connected to each other to define a pocket and further including the step of positioning the inner retainer member in a folded condition within the pocket of the outer jacket.

6. The method according to claim 1 wherein the cover panel includes a slot.

7. The method according to claim 6 wherein the step of positioning the suture end portions and the removable suture clip adjacent a rear side of the support panel includes receiving the suture end portions through the slot in the cover panel.

8. The method according to claim 1 wherein the step of attaching a removable suture clip to each suture end portion of the sutures includes bundling the sutures.

9. The method according to claim 1 wherein the step of attaching a removable suture clip to each suture end portion of the sutures includes spacing the sutures relative to one another.

10. The method according to claim 1 wherein the step of placing a plurality of sutures on the main support panel of the row of support panels includes simultaneously placing the sutures on the main support panel.

11. The method according to claim 10 wherein the sutures are arranged in a bundle.

12. The method according to claim 1 where in the suture clip is removable.

* * * * *